(12) United States Patent
Bellows et al.

(10) Patent No.: US 10,473,172 B2
(45) Date of Patent: Nov. 12, 2019

(54) BRAKE SCREW FOR SURGICAL LIGHTING SYSTEMS

(71) Applicant: American Sterilizer Company, Mentor, OH (US)

(72) Inventors: Lance Clark Bellows, Painesville, OH (US); Michael Joseph Heser, Willoughby, OH (US); Christopher Roy Mohr, Mentor, OH (US); Bernard John Moss, Perry, OH (US); Jerime Josef Pichler, Cleveland, OH (US); Cristian Laurentiu Toth, Independence, OH (US)

(73) Assignee: American Sterilizer Company, Mentor, OH (US)

( * ) Notice: Subject to any disclaimer, the term of this patent is extended or adjusted under 35 U.S.C. 154(b) by 26 days.

(21) Appl. No.: 16/004,499

(22) Filed: Jun. 11, 2018

(65) Prior Publication Data

US 2019/0011002 A1    Jan. 10, 2019

Related U.S. Application Data

(60) Provisional application No. 62/530,468, filed on Jul. 10, 2017.

(51) Int. Cl.
*F16B 21/00* (2006.01)
*F16D 65/06* (2006.01)
(Continued)

(52) U.S. Cl.
CPC ............. *F16D 65/06* (2013.01); *F16D 49/00* (2013.01); *F16D 65/0971* (2013.01); *F16D 2125/40* (2013.01)

(58) Field of Classification Search
CPC ..... F16B 41/002; F16B 5/0266; F16B 5/0208
(Continued)

(56) References Cited

U.S. PATENT DOCUMENTS 2,685,824 A    8/1954    Coop
3,159,075 A   12/1964    Bjork
(Continued)

FOREIGN PATENT DOCUMENTS

DE    20 2007 003 822 U1    6/2007
WO    WO 95/14176 A1        5/1995

OTHER PUBLICATIONS

Fastenerdata (Screw Protection Ends-Tips), Jun. 2, 2015, https://www.fastenerdata.co.uk/l16f22-tip; Fig. 2.

*Primary Examiner* — Christopher P Schwartz
(74) *Attorney, Agent, or Firm* — Kusner & Jaffe

(57) ABSTRACT

A brake screw for use with a surgical lighting system. The brake screw includes a screw member retained within a threaded aperture of a mounting hub of a spindle of an arm used with the lighting system. The screw member is rotationally adjusted to enable displacement in an axial direction. A brake member is in axial alignment with the screw member and disposed for movement in the axial direction against a mounting tube retained within the mounting hub upon rotational adjustment of the screw member. A rivet section is integrally formed with the brake member and has a distal end retained within an axial recess formed within the screw member, allowing movement of the brake member in the axial direction within the screw member. A bias member is disposed between the screw member and the brake member to create a biasing force that urges apart the screw member and the brake member along the axial direction.

22 Claims, 9 Drawing Sheets

(51) Int. Cl.
*F16D 49/00* (2006.01)
*F16D 65/097* (2006.01)
*F16D 125/40* (2012.01)

(58) Field of Classification Search
USPC .................................................. 411/352, 353
See application file for complete search history.

(56) References Cited

U.S. PATENT DOCUMENTS

| | | | | |
|---|---|---|---|---|
| 4,718,648 A * | 1/1988 | Taylor | ....................... | F16F 9/54 |
| | | | | 267/140 |
| 4,940,259 A | 7/1990 | Williams | | |
| 5,643,260 A | 7/1997 | Doherty | | |
| 5,702,217 A * | 12/1997 | Charbonnel | .......... | F16B 1/0014 |
| | | | | 411/259 |
| 5,851,095 A * | 12/1998 | Ellis | ..................... | F16B 41/002 |
| | | | | 411/353 |
| 6,095,736 A * | 8/2000 | Miller | ................... | F16B 41/002 |
| | | | | 411/107 |
| 6,135,321 A | 10/2000 | Hippensteel | | |
| 6,793,380 B2 | 9/2004 | Kupfer | | |
| 7,222,826 B1 | 5/2007 | Berglund | | |
| 7,938,607 B2 * | 5/2011 | Wang | .................... | F16B 5/0208 |
| | | | | 411/107 |
| 8,696,277 B2 * | 4/2014 | Wagner | ................ | F16B 41/002 |
| | | | | 411/108 |
| 8,920,063 B1 * | 12/2014 | Easley | ................. | F16B 21/165 |
| | | | | 269/48.1 |
| 9,347,471 B2 * | 5/2016 | Tseng | .................... | F16B 5/0208 |
| 2002/0159857 A1 | 10/2002 | McKinlay | | |
| 2004/0262484 A1 | 12/2004 | Wagner et al. | | |
| 2005/0242261 A1 | 11/2005 | Brahler et al. | | |
| 2011/0070049 A1* | 3/2011 | Wang | .................... | F16B 5/0208 |
| | | | | 411/372.6 |
| 2012/0224935 A1* | 9/2012 | Chiu | .................... | F16B 5/0266 |
| | | | | 411/352 |
| 2012/0237316 A1* | 9/2012 | Chiu | .................... | F16B 5/0208 |
| | | | | 411/353 |
| 2016/0208830 A1 | 7/2016 | Boyd et al. | | |
| 2017/0241587 A1 | 8/2017 | Timoszyk | | |

* cited by examiner

BRAKE SCREW FOR SURGICAL LIGHTING SYSTEMS

RELATED APPLICATIONS

This application claims the benefit of U.S. Provisional Application No. 62/530,468, filed Jul. 10, 2017, said provisional application is hereby fully incorporated herein by reference.

FIELD OF THE INVENTION

The present invention relates generally to an improved brake screw for use with surgical lighting systems.

BACKGROUND OF THE INVENTION

The majority of suspension systems for existing surgical lighting systems utilize mechanical radial braking devices in order to provide the required rotational performances of system components. The basic principle of these braking devices is that the force needed to achieve a desired level of friction/braking is applied in the radial direction (i.e., perpendicular to the axis of component rotation).

FIG. 1 illustrates an exemplary existing suspension system 10 for a surgical lighting system. Suspension system 10 is generally comprised of spindles 12 and arms 20. Spindles 12 include a mounting tube or ring 14. A first arm 20 includes a mounting hub 22 for mounting of the arm to a spindle 12. Arms 20 may also include a joint 24. A lighthead 35 is shown mounted to fourth arm 20.

FIGS. 2 and 3 illustrates an existing prior art brake screw 40 (i.e., M10×1 brake screw) used by several manufacturers of surgical lighting systems. Brake screw 40 is an assembly generally comprised of a screw member 42 (e.g., a steel screw member), a brake member 62 having a braking surface 64, and a bias member 72.

Screw member 42 includes a head section 44 and a rivet section 54. Head section 44 has a threaded outer surface 46 and a slot 48 dimensioned to receive a flathead screwdriver for rotational adjustment of brake screw 40. Rivet section 54 is integrally formed with screw member 42. Brake member 62 is ring-shaped, and thus there is an opening in the center of brake member 62. In the illustrated example, brake member 62 is made of a copper alloy material. Bias member 72 may take the form a biasing element, such as Belleville washers or a metal spring.

Brake screw 40 is available in several different sizes and is used to control rotational braking of various components of a surgical lighting system (e.g., horizontal/extension arms, spring arms, lightheads, monitor yokes, etc.).

As best seen in FIG. 2, brake screw 40 is installed into a mounting hub 22 of an arm, and is tightened to generate a radial/normal force against a curved surface 16 of a stationary mounting tube or ring 14 (or other stationary component of the suspension system). Initial contact between braking surface 64 of brake member 62 and curved outer surface 16 of mounting tube or ring 14 is a line contact. This requires a significant amount of radial force to achieve the frictional force large enough to prevent drifting of the rotating component (i.e., to balance the external moment around an axis of rotation). Overtightening and wearing of brake member 62 eventually causes rivet section 54 of brake screw 40 to become exposed. As a result, a surface of rivet section 54 comes into direct contact with curved outer surface 16 of mounting tube or ring 14. Since rivet section 54 has a smaller contact surface than braking surface 64, overtightening can cause rivet section 54 to dig into mounting tube or ring 14. Since the material of screw member 42 is harder than the material of mounting tube or ring 14, screw member 42 causes damage to mounting tube or ring 14, which is typically not a field replaceable/serviceable component.

It should be noted that braking surface 64 of brake member 62 is located very close to the tip of rivet section 54. When braking surface 64 of brake member 62 wears to the tip of rivet section 54, brake screw 40 becomes non-functional.

In the existing prior art brake screw 40, the area of braking surface 64 is limited due to the riveted method of attaching brake member 62 to screw member 42. This attachment method requires an opening at the center of braking member 62, which increases brake pressure, thereby accelerating wear of braking member 62.

Even when not overtightened, the linear wear limitation of brake member 62 is controlled by the thickness of the braking member 62 from braking surface 64 to the end of rivet section 54. In the case of brake screw 40 illustrated herein, this thickness is only 0.8 mm (0.031 in).

In view of the foregoing, there is a need for an improved brake screw that overcomes the drawbacks of prior art brake screws and has an extended useful life.

SUMMARY OF THE INVENTION

In accordance with a first aspect of the present invention, there is provided a brake screw, comprising: a screw member configured for retention within a threaded aperture of a mounting hub, for rotational adjustment to enable displacement in an axial direction; a brake member in axial alignment with the screw member and disposed for movement in the axial direction for engaging a mounting tube held within the mounting hub upon rotational adjustment of the screw member, wherein the brake member includes a braking surface that contacts an outer surface of the mounting tube; a rivet section integrally formed with the brake member and having a distal end retained within an axial recess formed within the screw member, allowing movement of the brake member in the axial direction within the screw member; and a bias member disposed between the screw member and the brake member to create a biasing force that urges apart the screw member and the brake member along the axial direction, to thereby apply a braking force between the braking surface of the brake member and the outer surface of the mounting tube, in order to retain the mounting tube in a fixed position.

In accordance with another aspect of the present invention, there is provided a brake screw, comprising: a screw member configured for retention within a threaded aperture of a mounting hub, for rotational adjustment to enable displacement in an axial direction; a brake member in axial alignment with the screw member and disposed for movement in the axial direction for engaging a mounting tube held within the mounting hub upon rotational adjustment of the screw member; a rivet section integrally formed with the screw member and having a distal end retained within an axial recess formed within the brake member, allowing movement of the screw member in the axial direction within the brake member; a removable brake cover including a brake element portion that includes a braking surface and an opposing surface that engages an underside of the brake member; and a bias member disposed between the screw member and the brake member to create a biasing force that urges apart the screw member and the brake member along the axial direction, to thereby apply a braking force between the braking surface of the removable brake cover and an outer surface of the mounting tube, in order to retain the mounting tube in a fixed position.

An advantage of the present invention is the provision of a brake screw that has improved wear properties.

Another advantage of the present invention is the provision of a brake screw having a brake member with increased braking surface area to eliminate the risk of screw based rivets damaging the mounting tube surface if the brake screws are overcompressed.

Still another advantage of the present invention is the provision of a brake screw having a brake member that reduces brake pressure, thereby reducing wear of the brake member and prolonging the life of the brake screw.

Still another advantage of the present invention is the provision of a brake screw having an assembly that allows the thickness of the brake member to be the limiting factor for brake screw wear, thereby improving the useful life of the brake screw.

Yet another advantage of the present invention is the provision of a brake screw having a brake member with a pre-curved braking surface, thereby eliminating the need for a break-in period where the braking surface must wear to match the curvature of a surface of a mounting tube or ring in order to maximize braking force.

These and other advantages will become apparent from the following description of illustrated embodiments taken together with the accompanying drawings and the appended claims.

BRIEF DESCRIPTION OF THE DRAWINGS

The invention may take physical form in certain parts and arrangement of parts, several embodiments of which will be described in detail in the specification and illustrated in the accompanying drawings which form a part hereof, and wherein.

DETAILED DESCRIPTION OF THE INVENTION

The drawings shown herein are for the purpose of illustrating embodiments of the invention only and not for the purposes of limiting same. It should be appreciated that the features of each disclosed embodiment may be combined in configurations alternative to those illustrated herein. It is intended that all such alternative configurations come within the scope of the present invention.

Several embodiments of a brake screw according to the present invention will be described in detail with reference to the FIGS. 4-18. As depicted in these drawings, the embodiments of the brake screw according to the present invention are generally comprised of a screw member, a brake member (e.g., a friction tip) having a braking surface, and a bias member (such as a spring).

Figure 1:
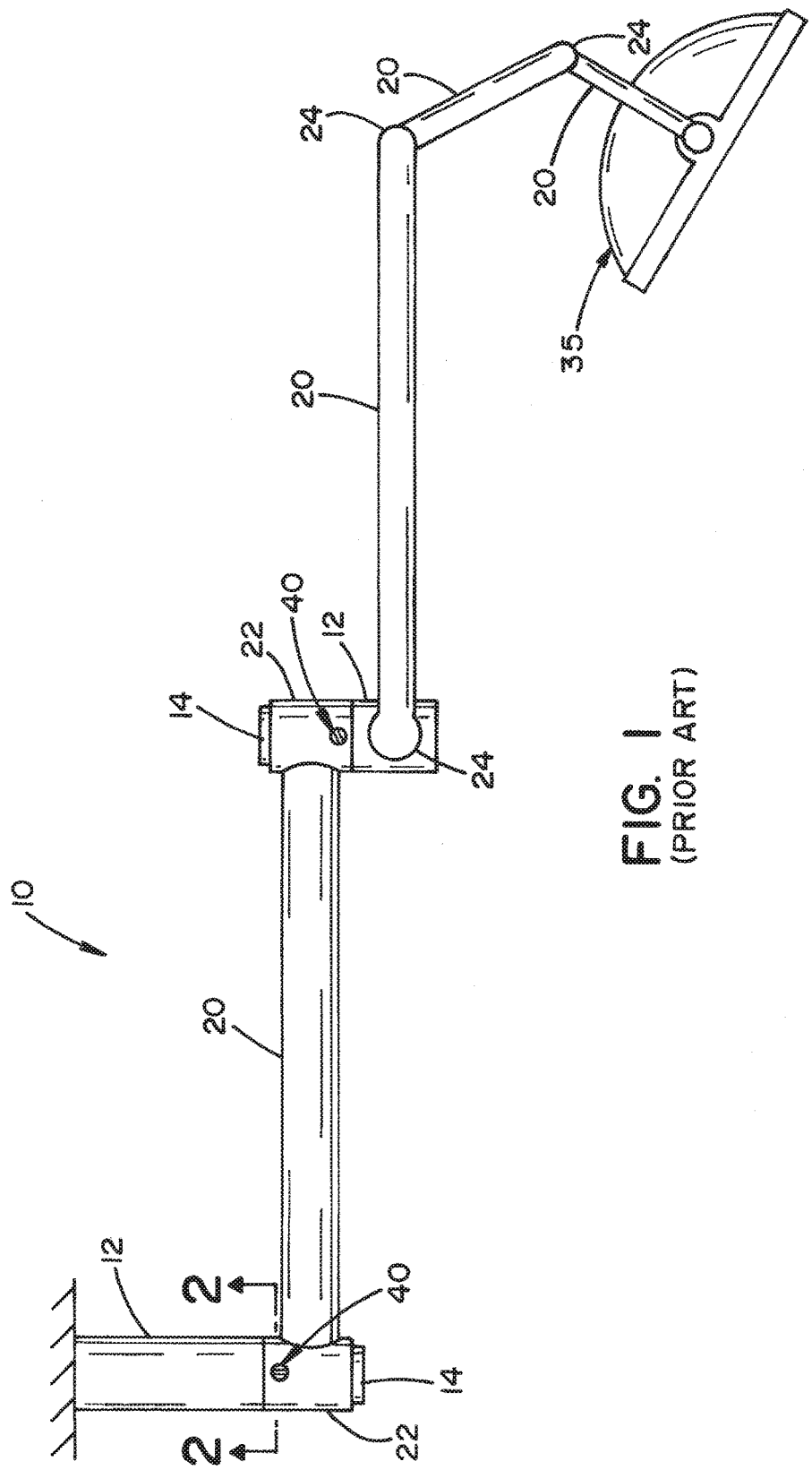
FIG. 1 illustrates an example suspension system for a surgical lighting system.
Figure 2:
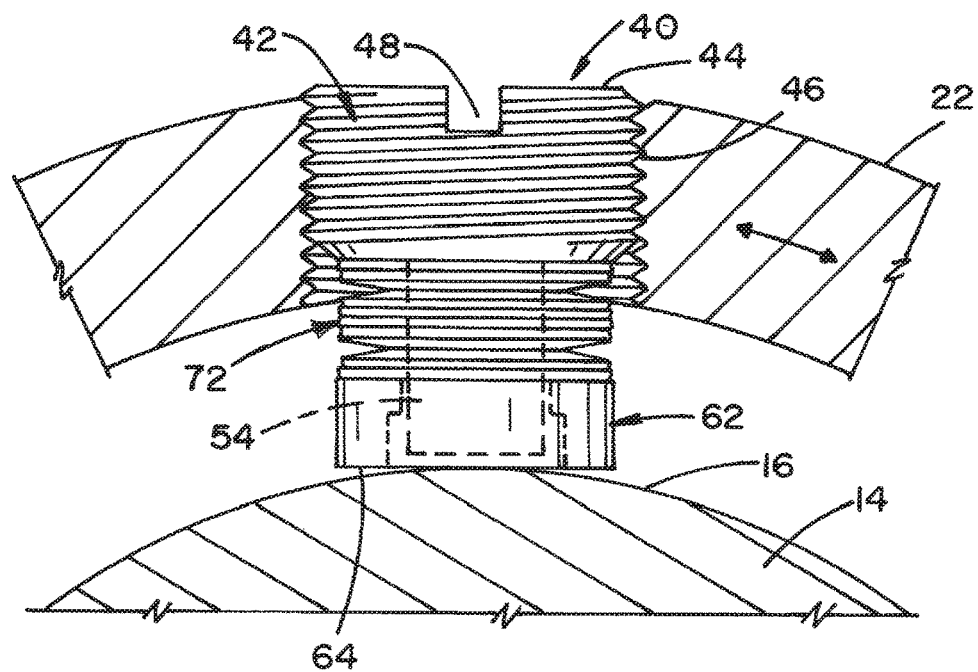
FIG. 2 is a cross-sectional view taken across lines 2-2 of FIG. 1, showing an installed prior art brake screw.

The embodiments of the brake screw shown in FIGS. 4-18 are implemented in accordance with a suspension for a surgical lighting system is depicted in FIGS. 1 and 2. The brake screw is used to control rotational braking of various components of a surgical lighting system (e.g., horizontal/extension arms, spring arms, lightheads, monitor yokes, etc.) and replaces the standard prior art M10×1 brake screw used by manufacturers of surgical lighting systems.

The brake screw is preferably installed into a threaded aperture formed in the sidewall of a mounting hub 22 used with a spindle 12 of an arm 20 in the suspension system 10. The brake screw is thereby securely retained in mounting hub 22. Rotational adjustment causes the brake screw to be displaced in an axial direction, that is, in the direction of a central axis A-A of the brake screw along which the components are aligned.

Rotational adjustment causes the brake screw to advance inward into the sidewall of mounting hub 22 in the direction of the radius of mounting hub 22 to bring the brake screw into mechanical engagement with a stationary mounting tube or ring 14 (or other stationary component of the suspension system 10), concentrically held and retained within the mounting hub 22. The brake screw is tightened to generate a radial/normal force against a curved surface 16 of stationary mounting tube 14, in order to retain mounting hub 22 (and thus arm 20) in a fixed position against movement.

Figure 3:
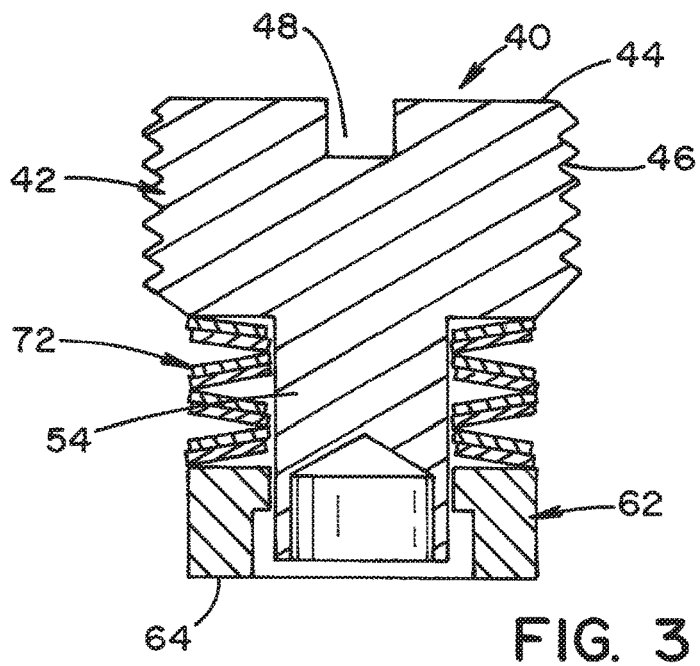
FIG. 3 is a cross-sectional view of the prior art brake screw shown in FIG. 2.

It should be appreciated that in the existing prior art brake screw 40, as illustrated in FIGS. 2 and 3, integral rivet section 54 of screw member 42 functions as a retaining element to hold brake member 62 and bias member 72 to screw member 42. In the embodiments of the brake screw shown in FIGS. 4-16 according to embodiments of the present invention, a brake member includes an integral rivet section that functions as a retaining element to hold the brake member and the bias member to the screw member. Accordingly, one important difference between the embodiments of the brake screw according to the present invention and brake screw 40 of the prior art is that the method for retention of the brake member to the screw member is reversed to improve the wear properties of the brake screw and to prevent screw based rivets from damaging the mounting tube surface if the brake screws are overcompressed.

Figure 4:
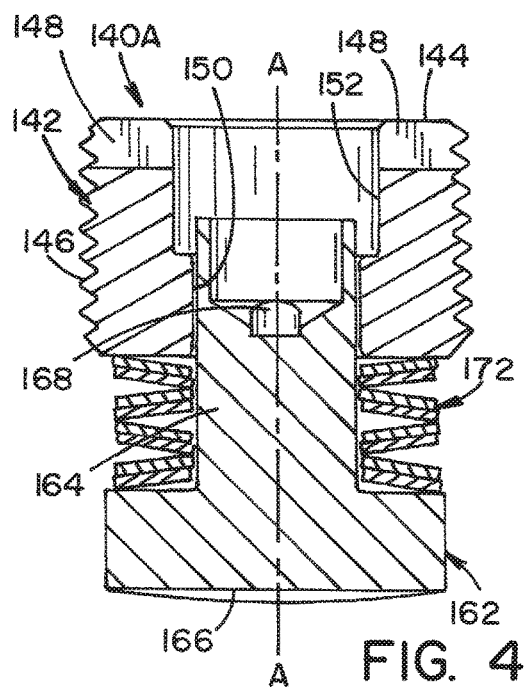
FIG. 4 is a cross-sectional view of a brake screw according to a first embodiment of the present invention.
Figure 5:
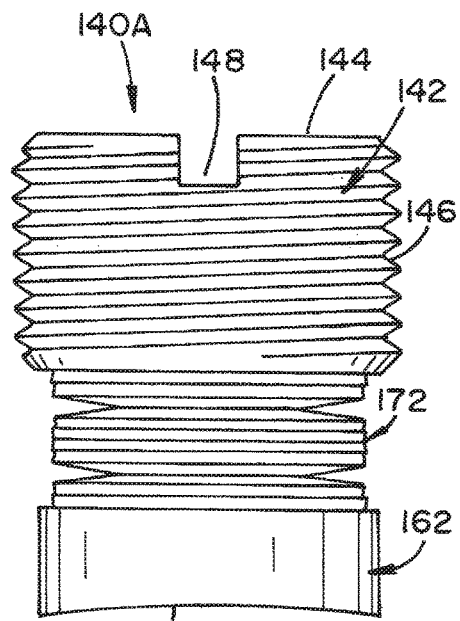
FIG. 5 is a side plane view of the brake screw shown in FIG. 4.
Figure 6:
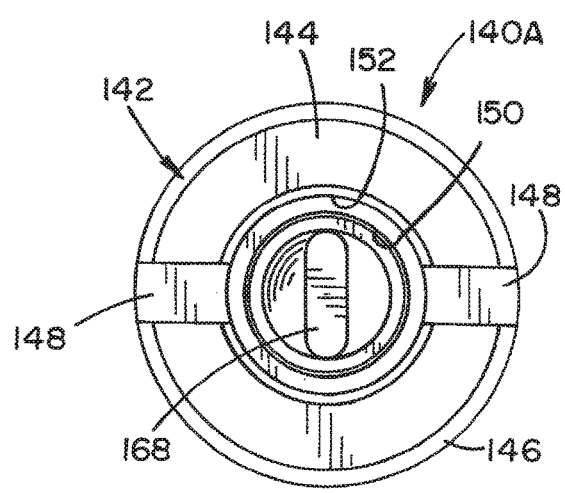
FIG. 6 is a top plan view of the brake screw shown in FIG. 4.

Referring now specifically to FIGS. 4-6, there is shown a brake screw 140A according to an embodiment of the present invention having a "reverse stake" design. A screw member 142 includes a head section 144 having a threaded outer surface 146 and a screw drive in the form of a slot 148 dimensioned to receive a mating driver tool (e.g., a flathead screwdriver) for rotational adjustment of brake screw 140A (i.e., tightening and loosening the brake screw within a corresponding threaded aperture in the sidewall of mounting hub 22 of arm 20 of suspension system 10 for a surgical light). It is also contemplated that any other suitable screw drive can be substituted for the flathead slot, such as a hexagonal socket recess, so that an Allen wrench can be used for rotational adjustment of the brake screw instead of a flathead screwdriver. Other suitable drives can alternatively be used including polygonal socket drives such as a square Robertson drive, a cruciform drive (e.g., a Phillips head), or a multi-polygonal (star) drive, all working with suitable mating tools. An axial recess 150 is formed along the central axis A-A in screw member 142. In the preferred embodiment, axial recess 150 is formed as a cylindrical bore. An axial aperture 152 is provided at the open end of screw member 142, adjoining axial recess 150 and having a greater diameter than axial recess 150.

A brake member 162 of brake screw 140A includes a rivet section 164 formed as an integral portion of brake member 162. Rivet section 164 is dimensioned to be received into axial recess 150 formed in screw member 142, preferably as a cylindrical shaft corresponding to the cylindrical bore. It should be appreciated that brake screw 140A of the embodiment shown in FIG. 4 eliminates the center opening of the brake member of prior art brake screws which causes increased brake pressure and wear of the brake member, as well as premature failure of the prior art brake screws due to overtightening.

Brake member 162 shown in FIGS. 4 and 5 has a pre-curved braking surface 166 that conforms to curved outer surface 16 of stationary mounting tube or ring 14 of suspension system 10. Pre-curved brake surface 166 is formed to enable mating contact with curved outer surface 16 and thereby eliminates the need for a "break-in" period for brake member 162 as has been necessary with existing prior art brake screws due to initial line contact with curved outer surface 16 of stationary mounting tube or ring 14.

Furthermore, screw member 142 shown in FIGS. 4-6 includes an index mark 168 that allows proper orientation of pre-curved braking surface 166 relative to curved outer surface 16 of stationary mounting tube or ring 14. Index mark 168 can be shaped to receive a flathead screwdriver for rotational adjustment of brake member 162. Such an index mark 168 can thus be formed as a slot drive, a lateral groove within a cylindrical recess on a distal surface of rivet section 164 received within head section 144. However, index mark 168 can alternatively be formed directly on the distal end surface of rivet section 164 and can be formed as any other suitable screw drive selected from one of a cruciform drive (Phillips), a polygonal socket drive (Allen or Robertson), a multi-polygonal star drive, or any other suitable tool head shape or other suitable implementation for effecting rotation. The distal end of rivet section 164 can be formed into a "swaged edge" that functions as a retaining element, as explained in detail hereinbelow in connection with FIGS. 15 and 16.

A bias member 172 of brake screw 140A of FIGS. 4-6 preferably takes the form of a Belleville washer stack. It is understood in the art that a Belleville washer has a frusto-conical shape and a central opening in order to be spring-loaded along its axis. This arrangement creates a biasing force that urges apart screw member 142 and brake member 162 along the axial direction of brake screw 140A (i.e., along central axis A-A as shown in FIG. 4), thereby applying a braking force between braking surface 166 of brake member 162 and curved outer surface 16 of mounting tube 14, in order to retain mounting tube 14 in a fixed position. It is to be appreciated that any other suitable type of biasing device can also be substituted for use as bias member 172, as will be explained below in connection with other embodiments.

Figure 7:
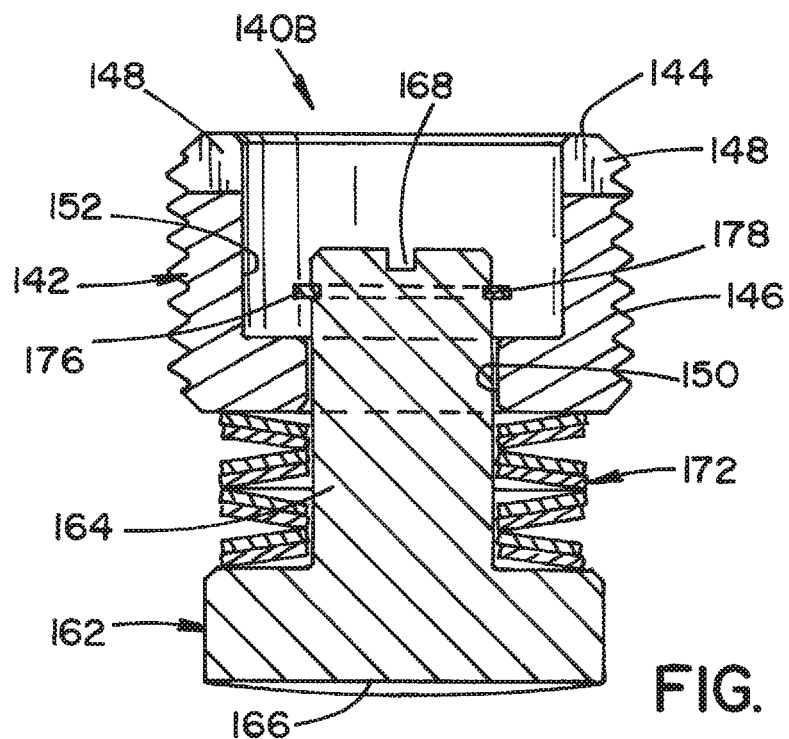
FIG. 7 is a cross-sectional view of a brake screw according to a second embodiment of the present invention.

The embodiment of brake screw 140B shown in FIG. 7 is similar to the embodiment of brake screw 140A shown in FIGS. 4-6, and includes similar corresponding elements as indicated by the corresponding reference numerals. The embodiment of FIG. 7 includes an index mark 168 formed directly on the distal surface of rivet section 164. The embodiment of FIG. 7 also includes a retaining ring 176 that functions as a retaining element to hold brake member 162 and bias member 172 to screw member 142. Such a retaining element is substantially proximate to the distal end of rivet section 164, having a diameter greater than rivet section 164, for delimiting movement of brake member 162 in the axial direction (i.e., along the central axis A-A shown in FIG. 4) and thereby preventing uncoupling of brake member 162 from screw member 142.

The retaining ring 176 of FIG. 7 is preferably a flat, circular, washer-like structure with a central aperture. The interior surface of retaining ring 176 is sized to be received within a circumferential groove 178 formed along the exterior surface of rivet section 164 near the distal end. The retaining ring 176 delimits the axial movement of brake member 162, thereby preventing uncoupling of screw member 142.

Figure 8:
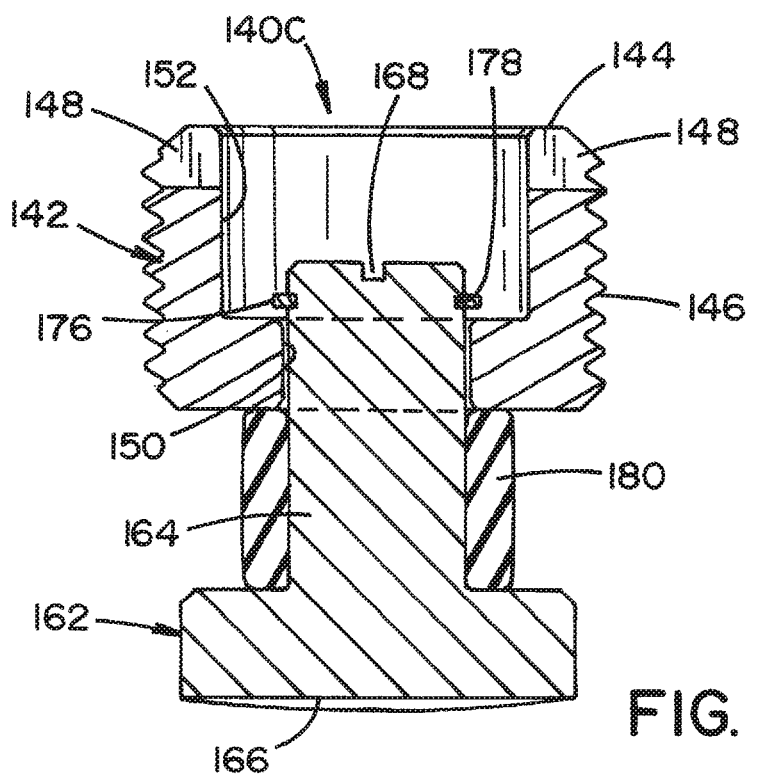
FIG. 8 is a cross-sectional view of a brake screw according to a third embodiment of the present invention.

The embodiment of brake screw 140C as shown in FIG. 8 is similar to the embodiment of brake screw 140B shown in FIG. 7, except that the bias member takes the form of an elastomeric member instead of a stack of Belleville washers. The elastomeric member includes a rubber bushing member 180 that applies an axial biasing force between the components of brake screw 140C. In particular, rubber bushing member 180 urges apart screw member 142 and brake member 162 along the axial direction of brake screw 140C (i.e., in the direction of central axis A-A shown in FIG. 4), thereby applying a braking force to curved outer surface 16 of stationary mounting tube or ring 14.

Figure 9:
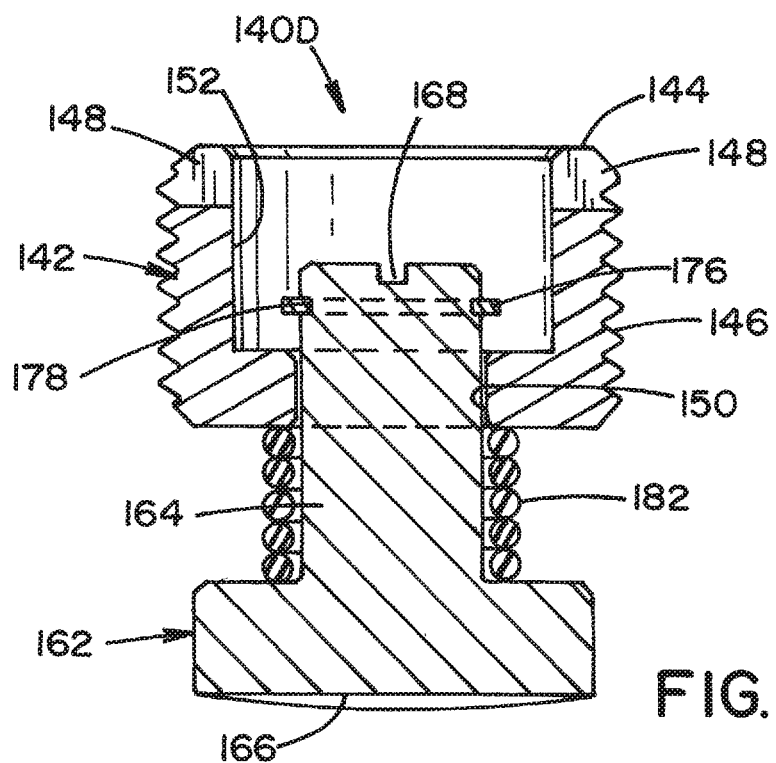
FIG. 9 is a cross-sectional view of a brake screw according to a fourth embodiment of the present invention.

The embodiment of brake screw 140D as shown in FIG. 9 is similar to the embodiment of brake screw 140C shown in FIG. 8, except that the elastomeric bias member takes the form of a stack of O-rings 182 instead of a rubber bushing. The stack of O-rings 182 applies an axial biasing force to the components of brake screw 140D. In particular, the stack of O-rings 182 urges apart screw member 142 and brake member 162 along the axial direction of brake screw 140D, thereby applying a braking force to the curved outer surface 16 of stationary mounting tube or ring 14. The magnitude of the axial force can be selectively adjusted by varying the size and number of O-rings. For example, a larger number of smaller-diameter O-rings can be selected, or a smaller number of larger diameter O-rings can be implemented.

Elastomeric materials can be selected that have greater or lesser elasticity, thus varying the compressive force.

Figure 10:
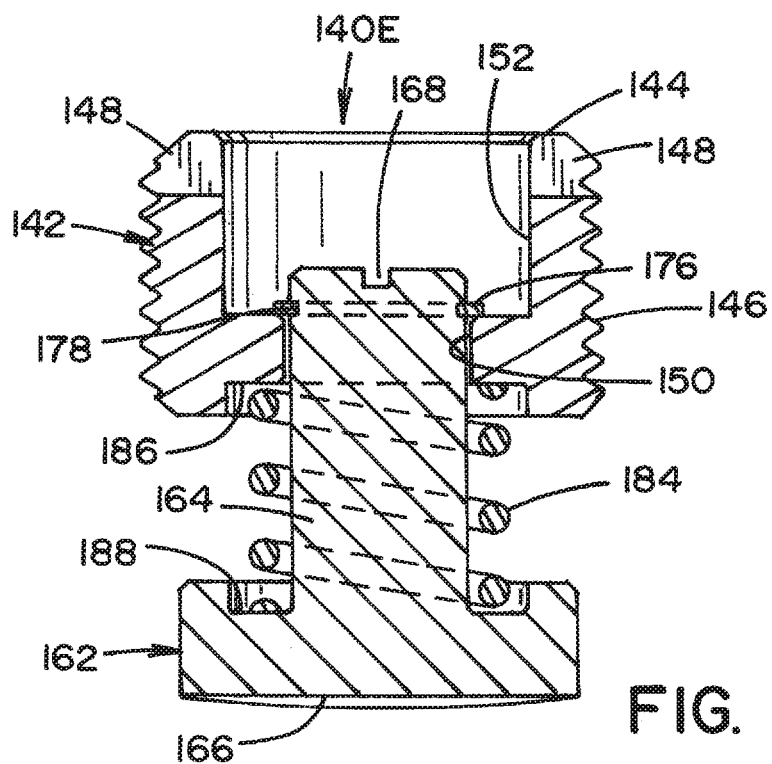
FIG. 10 is a cross-sectional view of a brake screw according to a fifth embodiment of the present invention.

The embodiment of brake screw 140E as shown in FIG. 10 is similar to the embodiment of brake screw 140B shown in FIG. 7, except that the bias member takes the form of a coil compression spring 184 instead of a stack of Belleville washers. Opposite ends of coil compression spring 184 are received and retained within a pair of annular recesses 186, 188. A first annular recess 186 is formed in a bottom surface of screw member 142 while a second annular recess 188 is formed on a top surface of brake member 162.

Figure 11:
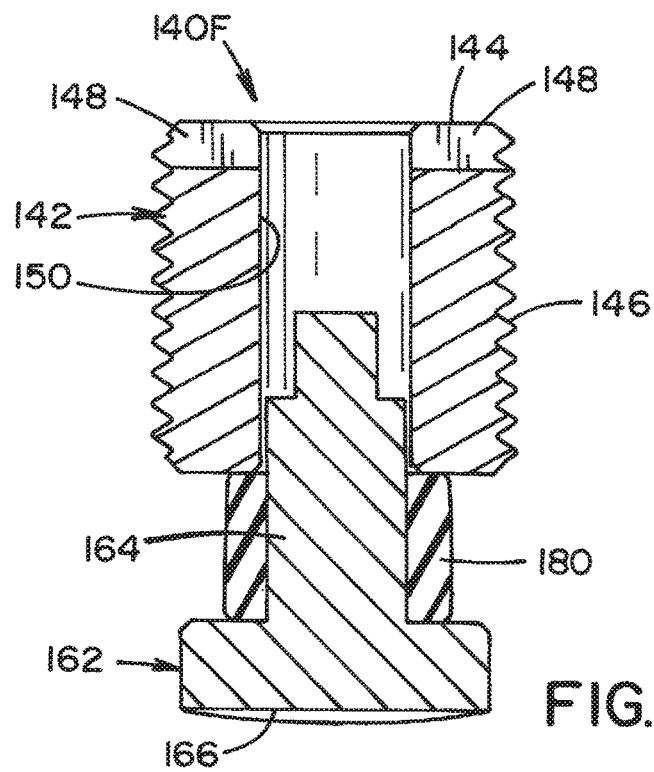
FIG. 11 is a cross-sectional view of a brake screw according to a sixth embodiment of the present invention.

Referring now to FIG. 11, there is shown an embodiment of brake screw 140F that is comprised of both free sliding and loose components. In this respect, no retaining element is used to hold together the components of brake screw 140F. Instead, the components are held together when brake screw 140F is installed in the suspension system of the surgical lighting system. However, the embodiment of FIG. 11 can be readily adapted to include a retaining element. As depicted, rivet section 164 includes a small diameter portion at the distal end which can be adapted to receive a retaining element in accordance with any of the other herein-disclosed embodiments. This illustrated embodiment of brake screw 140F depicts a bias member in the form of rubber bushing member 180 as shown in FIG. 8. However, it is to be appreciated that the bias member can also be implemented as either a stack of Belleville washers, a stack of O-rings, a coil compression spring, all as illustrated herewith, or any other suitable biasing member, as understood in the art.

Figure 12:
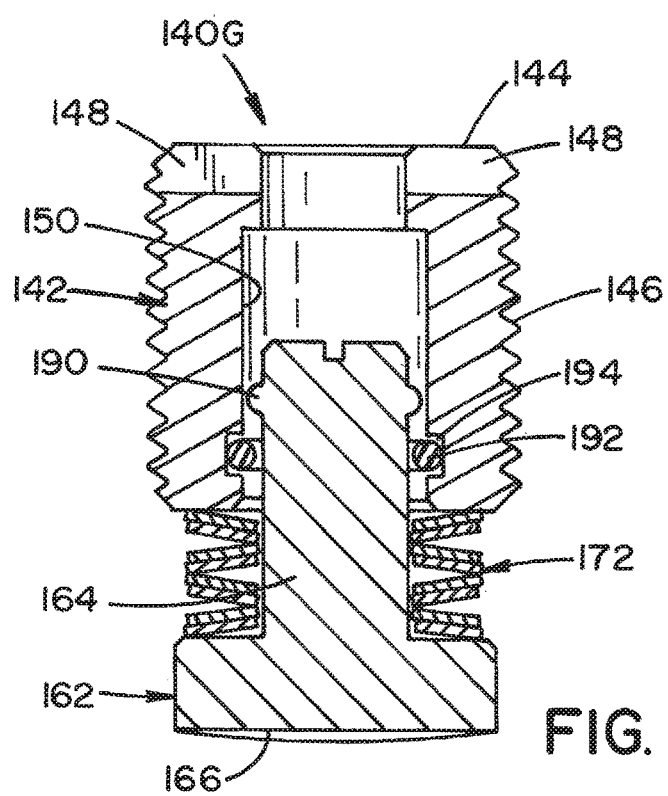
FIG. 12 is a cross-sectional view of a brake screw according to a seventh embodiment of the present invention.

The embodiment of brake screw 140G as shown in FIG. 12 is similar to the embodiments of the brake screw particularly shown in FIGS. 4-10, except that brake member 162 is retained on screw member 142 by an outward extending annular protrusion 190 (e.g., a rib) integrally formed on rivet section 164 of brake member 162. Rib 190 is provided instead of retaining ring 176 and is formed as an annular portion having a diameter greater than the diameter of rivet section 164 but less than the diameter of axial recess 150 of screw member 142. The axial motion of brake member 162 is restrained by an interaction of rib 190 with an O-ring 192 that is installed inside an annular recess 194 formed on the interior surface of axial recess 150 of screw member 142.

Figure 13:
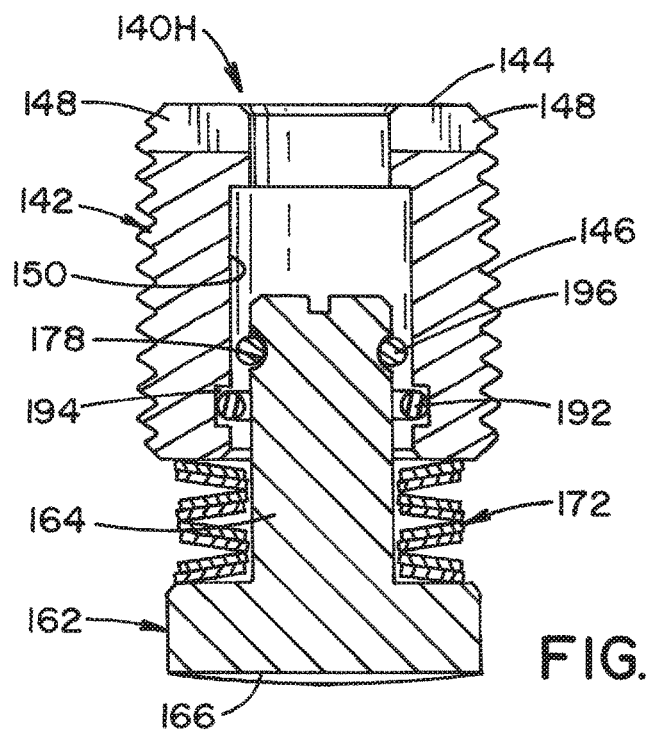
FIG. 13 is a cross-sectional view of a brake screw according to an eighth embodiment of the present invention.

The embodiment of brake screw 140H as shown in FIG. 13 is similar to the embodiment of brake screw 140G shown in FIG. 12, except that a wire retaining ring 196 replaces outward extending annular protrusion 190 formed on brake member 162. As with the embodiments of the brake screw depicted in FIGS. 7-10, wire retaining ring 196 is sized to be received within circumferential groove 178 formed along the exterior surface of rivet section 164 near the distal end.

Figure 14:
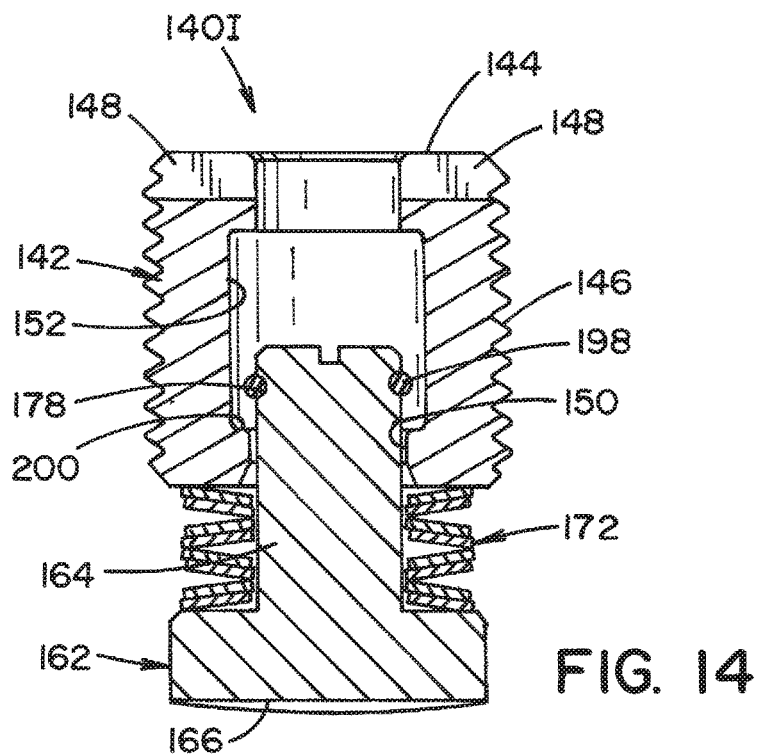
FIG. 14 is a cross-sectional view of a brake screw according to a ninth embodiment of the present invention.

The embodiment of brake screw 140I as shown in FIG. 14 is similar to the embodiments of the brake screw shown in FIGS. 7-10, except that brake member 162 is retained on screw member by an O-ring 198, received within circumferential groove 178 of rivet section 164 of brake member 162, and an undercut 200 formed at the bottom of axial aperture 152 of screw member 142, where axial aperture 152 adjoins the lower-diameter axial recess 150. The axial motion of brake member 162 is restrained by an interaction of O-ring 198 with undercut 200.

Figure 15:
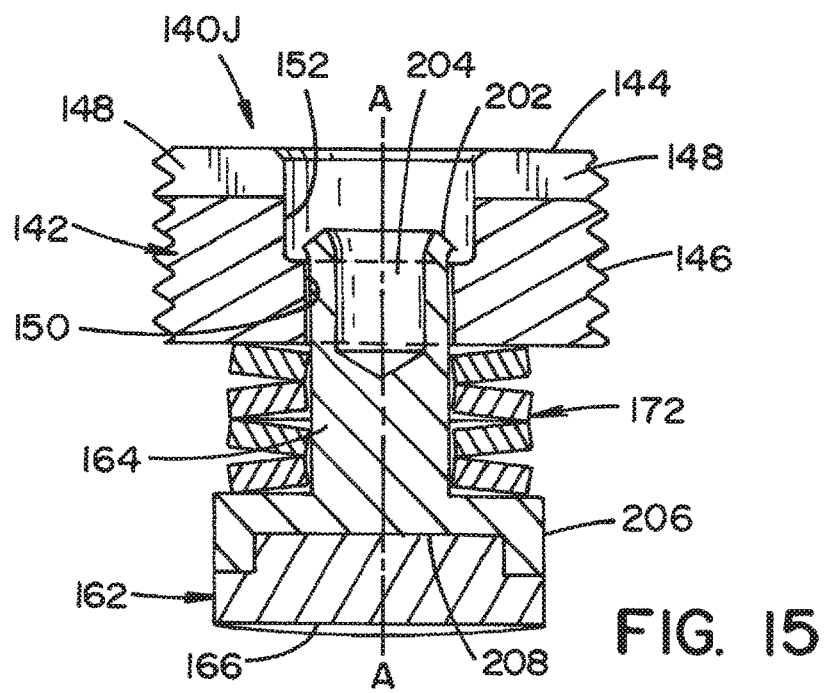
FIG. 15 is a cross-sectional view of a brake screw according to a tenth embodiment of the present invention.

The embodiment of brake screw 140J as shown in FIG. 15 is similar to the embodiment of brake screw 140A shown in FIGS. 4-6, except that the distal end of rivet section 164 is formed into a swaged edge 202 in place of a discrete retaining element. The distal end of rivet section 164 includes a cylindrical recess 204, which can be an axial bore.

Swaged edge 202 can be formed by using a punch to outwardly flare the edge of cylindrical recess 204 to form a lip or flange, in accordance with fabricating techniques commonly understood in the art.

Upon flaring the edge of cylindrical recess 204, the resulting swaged edge 202 has a diameter greater than rivet section 164 and axial recess 150. In this manner, swaged edge 202 functions in the same manner as the retaining element in the other disclosed embodiments to hold brake member 162 and bias member 172 to screw member 142, for delimiting movement of brake member 162 in the axial direction and thereby preventing uncoupling of brake member 162 from screw member 142.

As also depicted in the embodiment of FIG. 15, brake member 162 and rivet section 164 are integrally formed as a composite assembly of different metals. Brake member 162 is a discrete component formed of bronze and rivet section 164 is a separate, distinct component formed of stainless steel. The rivet section 164 includes a large diameter end 206, opposite from the distal end. Aperture 208 is formed within large diameter end 206, preferably axially centered. Brake member 162 is pressed into aperture 208, and securely retained with an interference fit. However, the brake member 162 can alternatively be retained within aperture 208 using a suitable bonding agent. In this manner, the softer bronze brake member 162 forms a suitable contact surface for engaging the mounting tube while the stronger stainless steel rivet section 164 possesses greater mechanical strength, avoiding the brittleness of a solid bronze component.

Figure 16:
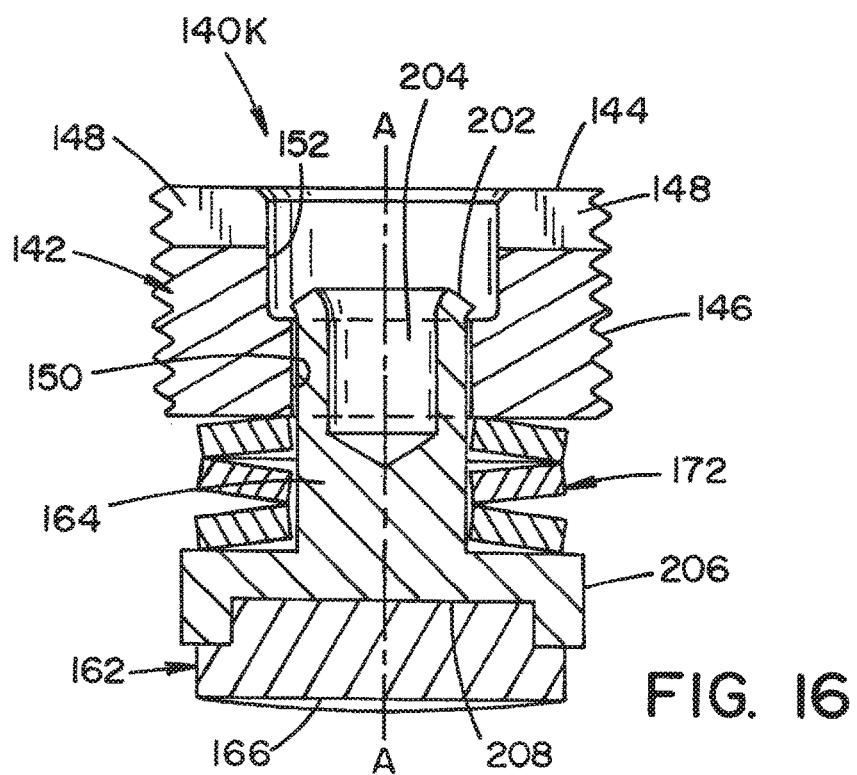
FIG. 16 is a cross-sectional view of a brake screw according to an eleventh embodiment of the present invention

The embodiment of brake screw 140K as shown in FIG. 16 is similar to the embodiment of brake screw 140J shown in FIG. 15, except that brake member 162 has a smaller diameter than the large diameter end 206 of rivet section 164.

Figure 17:
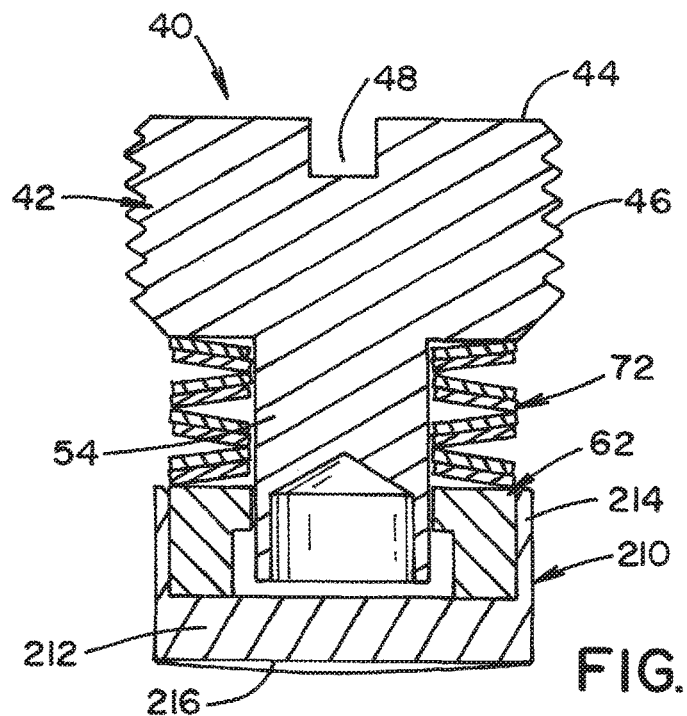
FIG. 17 is a cross-sectional view of a retrofit brake screw according to a twelfth embodiment of the present invention.
Figure 18:
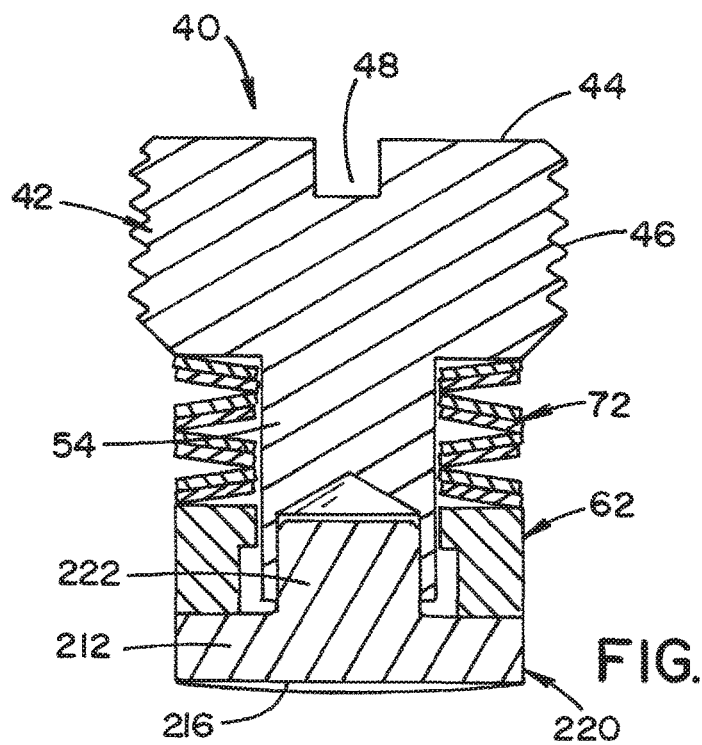
FIG. 18 is a cross-sectional view of a retrofit brake screw according to a thirteenth embodiment of the present invention.

FIGS. 17 and 18 depict brake screw embodiments according to the present invention that allow retrofitting to extend the useful life of current prior art brake screws 40 of the type such as those shown in FIGS. 2 and 3, in which like reference numerals refer to like elements. The embodiments of FIGS. 17 and 18 include rivet section 54 integrally formed with screw member 42 and having a distal end retained within an axial recess formed within brake member 62, allowing movement of brake member 62 in the axial direction around rivet section 54 of screw member 42.

According to the embodiment shown in FIG. 17, a removable brake cover 210 engages the brake member 62 of the prior art brake screw 40. Removable brake cover 210 includes a brake element portion 212 and a cylindrical wall portion 214. Brake element portion 212 includes pre-curved braking surface 216 and an opposing surface that engages an underside of brake member 62. The interior of cylindrical wall portion 214 defines a recess dimensioned to receive brake member 62 of the prior art brake screw 40. Accordingly, brake cover 210 fits over the outer diameter of the prior art brake member 62. Brake cover 210 may be made of a copper-based alloy. Upon tightening of brake screw 40 to apply a radial/normal force, brake cover 210 is urged with brake member 62 into contact with the mounting hub.

Removable brake cover 220 shown in FIG. 18 is similar to the embodiment shown in FIG. 17, except that cylindrical wall portion 214 is replaced with an extension portion 222, formed integrally with brake element portion 212, and dimensioned to be movably received within a recess of rivet section 54 of screw member 42. Brake element portion 212 of brake cover 220 includes pre-curved braking surface 216 and an opposing surface that engages an underside of brake member 62. Upon tightening of brake screw 40 to apply a radial/normal force, brake cover 220 is urged with brake member 62 into contact with mounting hub 14.

It should be appreciated that the present invention provides several improvements to existing prior art brake screws, including, but not limited to, a larger, full diameter brake surface on the brake member; a brake member with a pre-curved braking surface; a retention element that is integrated into the brake member; rubber springs used as a bias member; and a hexagonal socket receptacle.

The brake screw described herein can be used in connection with a wide variety of apparatus, including, but not limited to, surgical lighting systems and equipment management systems with ceiling mounted suspensions.

The foregoing describes specific embodiments of the present invention. It should be appreciated that these embodiments are described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A brake screw, comprising:
   a screw member configured for retention within a threaded aperture of a mounting hub, for rotational adjustment to enable displacement in an axial direction;
   a brake member in axial alignment with the screw member and disposed for movement in the axial direction for engaging a mounting tube held within the mounting hub upon rotational adjustment of the screw member, wherein the brake member includes a braking surface that contacts an outer surface of the mounting tube;
   a rivet section integrally formed with the brake member and having a distal end retained within an axial recess formed within the screw member, allowing movement of the brake member in the axial direction within the screw member; and
   a bias member disposed between the screw member and the brake member to create a biasing force that urges apart the screw member and the brake member along the axial direction, to thereby apply a braking force between the braking surface of the brake member and the outer surface of the mounting tube, in order to retain the mounting tube in a fixed position.

2. A brake screw according to claim 1, wherein the screw member further comprises a head section having a threaded outer surface that mates with the threaded aperture of the mounting hub, the head section further comprising a screw drive dimensioned to receive a mating driver tool for rotational adjustment of the brake screw.

3. A brake screw according to claim 2, wherein the screw drive is selected from one of a slot drive, a cruciform drive, a polygonal socket drive, or a multi-polygonal star drive.

4. A brake screw according to claim 1, wherein the braking surface is a pre-curved braking surface and wherein the outer surface of the mounting tube is a curved outer surface, wherein the pre-curved braking surface matches the curved outer surface of the mounting tube, to enable mating contact between the braking surface and the curved outer surface of the mounting tube.

5. A brake screw according to claim 1, further comprising an index mark formed as a screw drive on the distal end of the rivet section, the screw drive dimensioned to receive a mating driver tool for rotational adjustment of the brake member to orient the pre-curved braking surface into the mating contact with the curved outer surface of the mounting tube.

6. A brake screw according to claim 5, wherein the screw drive is selected from one of a slot drive, a cruciform drive, a polygonal socket drive, or a multi-polygonal star drive.

7. A brake screw according to claim 1, further comprising a retaining element, substantially proximate to the distal end of the rivet section, having a diameter greater than the rivet section, to hold the brake member and the bias member to the screw member, for delimiting movement of the brake member in the axial direction and thereby preventing uncoupling of the brake member from the screw member.

8. A brake screw according to claim 7, wherein the retaining element is a retaining ring received within a circumferential groove formed along an exterior surface of the rivet section substantially proximate to the distal end.

9. A brake screw according to claim 7, wherein the retaining ring is one of an elastomeric O-ring or a wire retaining ring.

10. A brake screw according to claim 7, wherein the retaining element is an outward extending annular protrusion, integrally formed with the rivet section, having a diameter greater than the diameter of the rivet section but less than the diameter of the axial recess of the screw member.

11. A brake screw according to claim 7, further comprising an elastomeric O-ring installed inside an annular recess formed on an interior surface of the axial recess of the screw member, for interacting with the retaining element to restrain axial motion of the brake member.

12. A brake screw according to claim 7, further comprising an undercut formed at the bottom of an axial aperture of the screw member, the axial aperture adjoining with the axial recess and having a greater diameter than the axial recess, for restraining axial motion of the brake member by an interaction of the retaining element with the undercut.

13. A brake screw according to claim 1, wherein the bias member comprises a central aperture which receives and substantially surrounds the rivet section, and includes opposing ends that contact the brake member and the screw member.

14. A brake screw according to claim 13, wherein the bias member comprises one of a stack of Belleville washers, at least one elastomeric member, or a coil spring.

15. A brake screw according to claim 1, further comprising a swaged edge formed on the distal end of the rivet section, said swaged edge having a diameter greater than the rivet section and the axial recess, functioning as a retaining element to hold the brake member and the bias member to the screw member, for delimiting movement of the brake member in the axial direction and thereby preventing uncoupling of the brake member from the screw member.

16. A brake screw according to claim 15, wherein the distal end of the rivet section comprises a cylindrical recess and wherein the swaged edge is formed by outwardly flaring the cylindrical recess.

17. A brake screw according to claim 1, wherein the brake member and the rivet section are integrally formed as a composite assembly of different metals.

18. A brake screw according to claim 17, wherein the brake member is formed of bronze and the rivet section is formed of stainless steel, wherein the brake member is pressed into an aperture formed within the rivet section.

19. A brake screw according to claim 1, wherein the mounting hub and the mounting ring are components of a spindle of a movable arm in a suspension for a surgical lighting system, wherein the brake screw controls rotational braking of the components within the spindle.

20. A brake screw, comprising:
- a screw member configured for retention within a threaded aperture of a mounting hub, for rotational adjustment to enable displacement in an axial direction;
- a brake member in axial alignment with the screw member and disposed for movement in the axial direction for engaging a mounting tube held within the mounting hub upon rotational adjustment of the screw member;
- a rivet section integrally formed with the screw member and having a distal end retained within an axial recess formed within the brake member, allowing movement of the brake member in the axial direction around the rivet section of the screw member;
- a removable brake cover including a brake element portion that includes a braking surface and an opposing surface that engages an underside of the brake member; and
- a bias member disposed between the screw member and the brake member to create a biasing force that urges apart the screw member and the brake member along the axial direction, to thereby apply a braking force between the braking surface of the removable brake cover and an outer surface of the mounting tube, in order to retain the mounting tube in a fixed position.

21. A brake screw according to claim 20, wherein the removable brake cover further comprises a cylindrical wall portion defining a recess dimensioned to fit over an outer diameter of the brake member.

22. A brake screw according to claim 20, wherein the removable brake cover further comprises an extension portion, formed integrally with the brake element portion, and dimensioned to be movably received within an axial recess of the rivet section.

* * * * *